US011610680B2

(12) United States Patent
Sandholm (10) Patent No.: US 11,610,680 B2
(45) Date of Patent: Mar. 21, 2023

(54) MEDICAL TREATMENT PLANNING VIA SEQUENTIAL GAMES

(71) Applicant: Tuomas W. Sandholm, Pittsburgh, PA (US)

(72) Inventor: Tuomas W. Sandholm, Pittsburgh, PA (US)

(*) Notice: Subject to any disclaimer, the term of this patent is extended or adjusted under 35 U.S.C. 154(b) by 369 days.

(21) Appl. No.: 16/876,649

(22) Filed: May 18, 2020

(65) Prior Publication Data

US 2020/0279650 A1 Sep. 3, 2020

Related U.S. Application Data

(63) Continuation of application No. 13/955,966, filed on Jul. 31, 2013, now abandoned.

(Continued)

(51) Int. Cl.
*G06N 5/04* (2006.01)
*A61B 5/02* (2006.01)
(Continued)

(52) U.S. Cl.
CPC ............. *G16H 50/20* (2018.01); *G16H 50/50* (2018.01); *G16H 20/10* (2018.01); *G16H 20/30* (2018.01); *G16H 20/60* (2018.01); *Y02A 90/10* (2018.01)

(58) Field of Classification Search
CPC ........ G16H 50/20; G16H 50/50; G16H 20/10; G16H 20/30; G16H 20/60; Y02A 90/10
See application file for complete search history.

(56) References Cited

U.S. PATENT DOCUMENTS

2005/0080462 A1* 4/2005 Jenkins .................. G16H 20/60
607/58
2007/0141527 A1* 6/2007 Kuo ....................... G16H 70/20
433/24
(Continued)

FOREIGN PATENT DOCUMENTS

WO 2012118825 A2 9/2012

OTHER PUBLICATIONS

Chen et al., "Tractable Objectives for Robust Policy Optimization", pp. 1-9, NIPS 2012.
(Continued)

*Primary Examiner* — Maroun P Kanaan
(74) *Attorney, Agent, or Firm* — Fox Rothschild LLP (57) ABSTRACT

A method and system for identifying a treatment plan identifies a description of a sequential game. The game is associated with treatment of a medical condition by a course of treatment or drug design. The description may include one or more possible treatment actions that a treater can take to treat the medical condition, and one or more possible medical condition actions that the medical condition can take. The system will identify a model for the sequential game, wherein the model is a large game associated with a large state space. The system may solve the model to generate a treatment plan for the medical condition, wherein the treatment plan includes a set of possible treatment actions. To accommodate the large state space, the system may divide processing steps so that at least some of the model solving is done by a graphics processing unit, while performing other functions via a central processing unit.

21 Claims, 4 Drawing Sheets

Related U.S. Application Data (60) Provisional application No. 61/677,477, filed on Jul. 31, 2012.

(51) Int. Cl.
  *G16H 50/20*   (2018.01)
  *G16H 50/50*   (2018.01)
  *G16H 20/10*   (2018.01)
  *G16H 20/30*   (2018.01)
  *G16H 20/60*   (2018.01)

(56) References Cited

U.S. PATENT DOCUMENTS

| | | | |
|---|---|---|---|
| 2007/0276270 A1* | 11/2007 | Tran | A61B 5/0022 600/508 |
| 2012/0046965 A1 | 2/2012 | Ryan et al. | |
| 2012/0047105 A1* | 2/2012 | Saigal | G16Z 99/00 706/54 |
| 2012/0253771 A1 | 10/2012 | Col et al. | |
| 2012/0259648 A1* | 10/2012 | Mallon | G16H 10/60 705/2 |

OTHER PUBLICATIONS

Kamichetty, "Structured Probabilistic Models of Proteins Across Spatial and Fitness Landscapes", CMU-CS-11-116, Mar. 2011, School of Computer Science, Carneigie Mellon University, Pittsburgh, PA 19213, copyright 2011 Hetunandan Kamichetty.

Perez-Breva et al., "Game theoretic Algorithms for Protein-DNA Binding," Proceedings of the Annual Conference on Neural Information Processing Systems (2006).

Shortreed et al., "Informing Sequential Clinical Decision-Making Through Reinforcement Learning: an Empirical Study", published online: Dec. 22, 2010, Mach Learn (2011) 84: 109-136.

Sandholm,"The State of Solving Large, Incomplete-Information Games, and Application to Poker," Amercian Association for the Advancement of Artificial Intelligence (Winter 2010).

Billings et al., "Game-tree Search with Addaptation in Ntochastic Imperfect-Information Games", Department of Computer Science, University of Alberta (2006).

Frey et al., "Prediciting resistance mutations using protein design algorithms," Proceedings of the national Academy of Sciences, 107(13)13707-13712 (Aug. 3, 2010).

Ganzfried and Sandholm, "Game Theory-Based Opponent Modeling in Large Imperfect-Information Games," Proc. of International Conference on Autonomous Agents and Multi-Agent Systems, pp. 533-540 (May 2-6, 2011).

Ganzfried and Sandholm, "Tartanian5: A Heads-Up No-Limit Texas Hold'em Poker-Playing Program;" Amercian Association for the Advancement of Artificial Intelligence (2012).

Ganzfried and Sandholm, "Safe Opponent Exploitation," ACM Conference on Electronic Commerce (EC) '12 at pp. 587-604 (Jun. 4-8, 2012).

Ganzfried, Sandholm and Waigh, "Strategy Purification and Thresholding: Effective Non-Equilibrium Approaches for Playing Large Games," Proceedings of the 11th International Conference on Autonomous Agents and Multiagent Systems (AAMAS 2012) (Jun. 4-8, 2012).

Hoehn et al., "Effective Short-Term Opponent Exploitation in Simplified Poker," Amercian Association for the Advancement of Artificial Intelligence (Jul. 2005).

Johanson et al, "Data Biased Robust Counter-Strategies," International Conference on Artificial Intelligence and Statistics (AISTATS) (2009).

Johanson et al, "Computing Robust Counter-Strategies," Proceedings of the Annual Conference on Neural Information processing Systems (2007).

McCracken et al., "Safe Strategies for Agent Modelling in Games," Amercian Association for the Advancement of Artificial Intelligence (2004).

Kroer, C. et al., "Limited Lookahead in Imperfect-Information Games", Computer Science Dept., Carnegie Mellon University.

Kroer, C. et al., "Sequential Planning for Steering Immune System Adaptation", Computer Science Dept., Carnegie Mellon University.

\* cited by examiner

MEDICAL TREATMENT PLANNING VIA SEQUENTIAL GAMES

RELATED APPLICATIONS AND CLAIM OF PRIORITY

This patent document claims priority to, and is a continuation-in-part of, U.S. patent application Ser. No. 13/955,966, filed Jul. 31, 2013 and titled "Medical Treatment Planning via Sequential Games," which in turn claims priority to U.S. Provisional Patent Application No. 61/677,477, filed Jul. 31, 2012 and titled "Drug Design and Treatment Planning via Sequential Games." The disclosures of each priority application are fully incorporated into this document by reference.

BACKGROUND

When a medical professional such as a doctor, therapist or other medical professional (each of which may be referred to as a "doctor" in this document) meets with a patient, the doctor may assess the patient and arrive at a diagnosis for a medical condition. To address the condition, the doctor will develop and implement a course of treatment, which may include the administration of drugs, surgical procedures, additional tests, physical or mental therapy, lifestyle changes such as diet or activity restrictions, or other treatment elements.

With the advent of personalized medicine, computer-assisted methods and systems for identifying courses of treatment are increasingly being used. However, such methods and systems are typically limited to checklists and questionnaires that guide the medical professional through a series of questions in a decision tree type format. Such systems do not allow for consideration of external factors that are not already programmed into the system. Also, they are not able to account for the inherent uncertainties that can exist in some medical conditions.

Further, many medical conditions do not remain static over time. As the doctor and patient implement the course of treatment, the condition may improve, or it may become worse. In addition, additional medical conditions may arise, or the condition may not remain static despite the fact that the treatment is expected to improve the condition. Existing systems for identifying courses of treatment typically can only identify an entire course of treatment, and cannot self-adjust based on how the course of treatment affects the patient over time.

Thus, improved methods of identifying and designing pharmaceutical or other courses of treatment are desirable. This document describes methods and systems that are directed to solving some or all of these issues.

SUMMARY

This document describes methods and systems that use sequential game models, and algorithms for solving them, for drug design and/or treatment planning, such as treatment of a patient over time. In some of the embodiments described below, the treating party may establish "traps" that seems promising for the adversary (e.g., a disease), such that as the disease evolves over time into a trap, the treating party may be able to successfully attack the disease.

In various embodiments described in this document, a system for developing a course of treatment for a medical condition may include a central processing unit (CPU), a graphics processing unit (GPU), a user interface, a communication port and a non-transitory, computer-readable memory comprising one or more programming instructions that, when executed, will cause one or more of the processors to develop the course of treatment. To do this, the processors will identify a description of a sequential game by receiving, via the user interface or the communication port, information corresponding to a medical condition. The system will identify a set of possible treatment actions that a treater can take to treat the medical condition, and a plurality of sequences for the actions. For each of the plurality of sequences, the system will identify one or more possible medical condition actions that the medical condition can take in response to one or more of the possible treatment actions. The system will identify a model for the sequential game, wherein the game is a large game associated with a large state space, the model represents implementation of the possible treatment actions as moves in the sequential game in the large state space, and the model represents the possible medical condition actions in one or more sequences. The system will solve the model by applying a game-solving algorithm to the model to generate a treatment plan for the medical condition, where the treatment plan comprises a set of possible treatment actions. The system will then output a report of the treatment plan. The actions of identifying the possible treatment actions, the possible medical condition actions and the model will be implemented by the CPU. However, solving the model will be implemented, at least in part, by the GPU.

Optionally, when solving the model, the system may generate one or more contingent plans in the model.

Optionally, the treatment plan may include randomization via behavioral or mixed strategies.

Optionally, when solving the model to generate the treatment plan for the medical condition, the system may generate a treatment plan comprising one or more traps, where the medical condition is likely to take actions so as to fall into a trap that causes the medical condition to go into one or more of the following: (a) a state in which the medical condition may be more easily treated; (b) a state in which the medical condition is less virulent; (c) a state in which the medical condition is less contagious; or (d) a state from where the medical condition is less likely to evolve into a harmful state.

Optionally, when solving the model the system may apply an opponent model in which the medical condition is able to look ahead at most a set number of steps in the game. The system also may create a path for the medical condition in which a sequence of steps includes one or more steps within the set number that are attractive to the medical condition, and at least one step beyond the set number that is associated with a state of the medical condition that is better for the treater, a patient with the medical condition, or both.

Optionally, the one or more possible treatment actions that a treater can take to treat the medical condition may include one or more possible treatment actions that a treater can take to treat the medical condition at an individual level, a molecular level, or a population level. For example, the possible treatment action(s) may include action(s) to treat the medical condition at a molecular level by one or more of the following: (i) prescribing or administering one or more drugs to a patient having the medical condition; (ii) identifying a de novo drug; (iii) performing a surgical procedure on the patient having the medical condition; (iv) applying a therapy to the patient; (v) prescribing a lifestyle change to the patient; (vi) admitting the patient to a treatment facility;

(vii) releasing the patient from the treatment facility; (viii) taking one or more measurements of the patient; or (ix) taking no action.

Optionally, the description of the sequential game may include one or more possible nature actions that a nature player may take relating to treatment of the medical condition. Each possible nature action will be associated with a probability. The model may then represent occurrence of the possible treatment actions, the possible medical condition actions and the possible nature actions in the one or more sequences.

Optionally, when solving the model the system may use one or more game theory solution concepts and one or more utilities that are associated with outcomes, intermediate states, or transitions in sequential game play.

Optionally, when solving the model the system may implement an opponent modeling technique and exploit an opponent as the opponent model is improved over time based on experience. In addition or alternatively, the system may implement an opponent exploitation technique.

Optionally, the system may use information learned while using results of the model to develop an updated model.

Optionally, when solving the model the system may compute a best-response strategy to an opponent model using stochastic programming. The use of stochastic programming will include using a sample trajectory-based optimization and/or a policy gradient algorithm.

Optionally, when solving the model the system may implement an equilibrium finding technique comprising any of the following: Nash equilibrium, subgame perfect equilibrium, perfect Bayesian equilibrium, sequential equilibrium, trembling-hand perfect equilibrium, extensive-form perfect equilibrium, extensive-form proper equilibrium, admissible strategies, normal form perfect equilibrium, quasi-perfect equilibrium, normal form proper equilibrium, or correlated equilibrium.

In other embodiments, a system develops a course of treatment for a patient population in a pandemic. The system includes one or more processors, which in some embodiments may include a CPU and a GPU. The system also includes a user interface, a communication port, and a non-transitory, computer-readable memory comprising one or more programming instructions. The instructions, when executed, will cause one or more of the processors to receive, via the user interface or the communication port, information corresponding to an epidemic that may affect a population. The instructions also will cause the processor(s) to identify a set of possible treatment actions that a treater can take to treat a medical condition that arises in the epidemic, and also identify a plurality of sequences for the possible treatment actions, wherein the possible treatment actions comprise a vaccine and quarantining. For each of the sequences, the system will identify possible medical condition actions that the epidemic may take in the population in response to one or more of the possible treatment actions. The possible medical condition actions may include a number of patients with a complete recovery, a number of patients who require hospitalization and a number of patients who do not recover. The system will identify a model for a sequential game, wherein: (i) the game is a large game associated with a large state space; (ii) the model represents implementation of the possible treatment actions as moves in the sequential game in the large state space; and (iii) the model represents the possible medical condition actions in one or more sequences. The system will solve the model by applying a game-solving algorithm to the model to generate a treatment plan for the medical condition, where the treatment plan comprises a set of possible treatment actions, and it will output a report of the treatment plan. In these embodiments, the medical condition actions also may include a mutation of a strain of virus that is a cause of the epidemic. In addition, the instructions to identify the possible treatment actions, the possible medical condition actions and the model may be implemented by the CPU, while at least some of the instructions to solve the model may be implemented by the GPU.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

In this document, the terms "computing device" and "processor" refer to a computer or other machine that performs one or more operations according to one or more programming instructions. Examples of computing devices include desktop computers, laptop computer, electronic tablets, ultrabooks, smart phones, smart televisions, and similar electronic devices having processing and user interface capability. Various elements of an example of a computing device or processor are described below in reference to FIG. 3.

The embodiments described below include methods and systems that use sequential game models and algorithms for solving them, for drug design, dosage regimen planning and/or medical treatment planning. The models may be used to model how various courses of treatment may affect a medical condition over time, as well as how external factors can alter a course of treatment's ability to treat a medical condition.

In an embodiment, a medical condition may be a physical, physiological, mental or psychological condition of a patient. For example, a medical condition may refer to an illness or disease such as, for example, HIV, cancer, influenza, malaria, diabetes or schizophrenia. In an embodiment, a medical condition may refer to malnutrition, obesity and/or the like. A medical condition may be referred to in this document as a disease or illness.

In an embodiment, a treater is an entity that treats at least a portion of a medical condition. The treater may be a system that has sensors and effectors that take measurements and/or apply treatments autonomously. Hybrids are also possible where some of the measurements and treatments are done autonomously and others by humans, but still planned using the automated system described in this patent application. So, humans can serve as some of the sensors and effectors of the automated system. Examples include, without limitation, a nurse, a doctor or other healthcare professional. In an embodiment, a treater may be a patient if the patient self-treats, or a pharmaceutical company if the company is developing drugs or drug regimens for administration to one or more patients. In the context of this document, a treater may be an actual player who participates in a game and takes the actions of a treater, or it may be a virtual treater represented by the actions of a treater as automatically implemented by a system that is playing the game.

For example, consider an example of a patient who is being treated by a treater for a medical condition. The treater's task may be to treat the patient over time. The treatments may include applying various drug regimens or combinations of drugs; performing a surgical procedure; applying physical, mental or other therapy to the patient; prescribing a lifestyle change such as an exercise plan or dietary change or restriction, and so on.

In an embodiment, the state of the disease may change over time. For example, if the patient is diagnosed with HIV, it is known that the HIV virus may mutate over time. How the disease changes over time can be affected by the course of treatment.

To address issues such as this, this document describes modeling a course of treatment over time as a game. The particular model used may vary, and there may be many alternative ways of modeling the state of the disease, the space of possible treatments, and how the treatments affect the disease and the patient over time.

The game may include sequential and/or simultaneous moves, and it may have complete or incomplete information about the disease. Incomplete information can represent the treater's lack of exact knowledge about what moves the disease has taken so far in the game. For example, the treater may not know all the mutations that an HIV virus has taken. Similarly, there may be (e.g., for the disease) incomplete information about what treatment actions have been taken. Furthermore, there can be various forms of stochasticity in the game, as will be described below. Solving the game model would be expected to provide a good treatment plan. For example, if the course of treatment includes various drug designs or regimens, then if the course of treatment "wins" over the disease in the game, or optionally even if the course of treatment scores a partial victory (such as by improving the quality of life of the patient and/or extending the life of the patient), then the course of treatment may be considered to be a good one. Any now or hereafter known algorithm for solving a game model may be used. Examples include those that have been developed for solving various forms of poker in the incomplete-information game case. For instance, a leading approach for finding strong strategies for poker is to run an abstraction algorithm first (for information abstraction, action abstraction, phase abstraction, time abstraction, and/or other abstraction) to construct a game that is strategically equivalent or nearly equivalent but smaller and thus easier to solve, and then running an equilibrium-finding algorithm (such as counterfactual regret minimization, excessive gap technique, fictitious play, etc.) on the abstracted game to find strategies for the players according to some solution concept. Examples also include algorithms that have been developed for solving various forms of complete-information games such as chess, checkers, Go, and general game playing (for which there is an annual competition for computers). These include minmax search, $\alpha\beta$-pruning, proof number search, conspiracy numbers, transposition tables, endgame tables (e.g., via dynamic programming-like approaches), expectimax search, Monte Carlo tree search (e.g., Upper Confidence bounds applied to Trees (UCT) and variations thereof), and so on. In some embodiments, the system may be agnostic to the solving methodology.

Abstraction techniques may be especially useful if the present approach is used in large games (e.g., large state or action spaces). For example, in de novo drug design, the space of possible molecules is huge—even if molecules that are highly unlikely to work are removed from consideration up front, so action abstraction (i.e., bundling multiple actions into one representative one) can be useful for scalability.

One idea is that in order to solve game models in the context of systems described in this document, one can use incremental abstraction where the steps of abstraction and solving of the abstracted game are iterated (interleaved) multiple times. This way the solution of the game can inform where in the game model finer-grained abstraction is needed (and/or is affordable from a scalability perspective) and where the abstraction can be and/or needs to be coarsened. Note that abstraction and iterated abstraction can be used both when solving the game model using a game-theoretic solution concept and when solving the game model using opponent modeling/opponent exploitation.

One abstraction-related idea here is to make the actions in the game model higher-level concepts so as to reduce the size of the game model and make it more tractable (e.g., faster and/or less demanding in memory) to solve. In one embodiment, these higher-level actions can be behaviors, e.g., short or simple plans or plan snippets. In another embodiment, for example for drug design, the actions can include adding or subtracting bigger pieces than individual atoms (such as chains, cycles, groups, or even bigger pieces) to and from the drug molecule. This will support more scalable de novo drug design with the system described in this application. It can also be used to modify existing drug molecules instead of having to build them from scratch. This would also make the system more scalable for designing somewhat different drug molecules for different patient subpopulations—or even individuals—with different variants of a disease.

During the sequential and/or simultaneous moves of game play, the treater may implement any suitable treatment action, such as prescribing and/or administering one or more drugs or drug cocktails, exercise or therapy regimens or other treatment actions for the patient; admitting the patient to a treatment facility; releasing the patient from a treatment facility; measuring one or more aspects of the patient (such as pulse, heart rate, cholesterol level, structure and quantity of viruses and bacteria, and so on); or choosing to take no action for a period of time and/or until the disease takes its next action.

The treater can also use a strategy that tries to trap the opponent (adversary, e.g., a disease) with one or more traps. The goal is that disease moves (e.g., evolves) over time into a trap state that seems promising to the disease, but instead is a state such that the treater can successfully attack the disease. For instance, the treater can use an opponent model to model how the opponent is likely to play irrationally into a trap. For example, consider an opponent (disease) that cannot look ahead more than a set number (k) of steps in the game tree. In that setting, the treater can make the disease go down a patent that is eventually good for the treater by using a treatment strategy such that the early parts within the lookahead horizon (i.e., the set number k of steps) of the trap paths (e.g., all of them, most of them, or a high-probability set of them) are desirable to the disease (e.g., they have high utilities, discussed below, for the disease), but such that the later parts beyond the lookahead horizon of those paths (all, most, or a high-probability set of them) beyond the set number of steps are good for the treater and/or the patient.

For example, if we let k be the lookahead of Player 1, and $S_{I,a}^k$ be the nodes at lookahead depth k below information set I that are reachable (through some path) by action a. Player 1 has a node evaluation function h: $S \to \mathbb{R}$ that assigns a heuristic numerical value to each node in the game tree. Given a strategy $\sigma_r$ for the other player and fixed action probabilities for Nature, Player 1 chooses, at any given information set $I \in \mathfrak{T}_I$ at depth i, a (possibly mixed) strategy whose support is contained in the set of actions that maximize the expected value of the heuristic function at depth i+k, assuming optimal hypothetical play by her ($\max_{\sigma_l}$ in the formula below). We will denote this set by $$A_I^* = \left\{ a : a \in \operatorname*{argmax}_{a \in A_I} \max_{\sigma_I} \sum_{s \in I} \frac{\pi^{\sigma-1}(s)}{\pi^{\sigma-1}(I)} \sum_{s' \in S_{I,a}^k} \pi^\sigma(t_a^s, s') h(s') \right\},$$

where $\sigma = \{\sigma_l, \sigma_r\}$ is the strategy profile for the two players. Here moves by Nature are also counted toward the depth of the lookahead. The model is flexible as to how the rational player chooses $\sigma_r$ and how the limited-lookahead player chooses a (possibly mixed) strategy with supports within the sets $A^*_I$. For one, we can have these choices be made for both players simultaneously according to the Nash equilibrium solution concept. As another example, we can ask how the players should make those choices if one of the players gets to make, and commit to, all her choices before the other.

The opponent model can also include different lookahead capability for the opponent down different paths of the game tree, that is, the opponent may be able to look ahead deeper on some paths than others.

Note that when the game is played down a path, the treater may take actions that temporarily make the patient worse in order to achieve a better end result for the treater and/or patient. For example, in the context of HIV, the treater may use drug cocktails in the early parts of the game that are likely to cause the virus to mutate in directions that are not immediately better for the patient, but which can be tackled effectively in later parts of the paths with other drugs. Note that this is in stark contrast with must current practices where treatments are selected in order to myopically improve the patient's health. When the treater's possible actions include de novo (drug) molecules, the plan (treater's strategy) that the system outputs may include de novo drugs (which may be referred to as "trap drugs") whose main role is to trap the disease rather than immediately making the patient better.

For example, if a medical condition is a certain disease, then a trap may be a state in which the disease can be destroyed, become less powerful, become less virulent, become less contagious, or cannot (or is less likely to) evolve in a malicious way. As an example, a trap may be a first drug or a treatment regimen that makes one or more aspects of the patient's condition worsen for a short period of time, or which allows the disease to flourish for a short period of time, but which—after implementation—enables the treater to select a second drug or treatment regimen that will significantly improve the patient's health.

In an embodiment, the system may be applied at one or more levels to battle a disease. For example, the system may be applied at an individual level, at a molecular level and/or at a population level. This document will describe various embodiments within each level, but the examples are not to be considered restrictive.

Applying the system at an individual level may involve the treatment of an individual patient. For instance, consider the treatment of a patient who is infected with the HIV virus. At any point in the game, the treater may take one or more actions such as: (i) applying one or more treatments (such as which drug or drug cocktail mixture to use, when to bring the patient to hospital, when to release the patient, and/or the like), (ii) taking one or more measurements (such as measurements associated with a blood test or external observations such as weight and pulse), (iii) performing other actions; and/or (iv) taking no action. At each point in the game, the disease (e.g., HIV) may take one or more actions such as evolving the disease within the patient (e.g., evolving the pool of different forms of HIV viruses existing in the patient), making the patient worse or better in various ways, or taking no action.

When solving a game, the system may apply a game-solving algorithm to a model with one or more utilities. A utility is a representation of a player's welfare at any point in the game. In some embodiments, utilities may be associated with one or more outcomes, intermediate states, and/or transitions in the game. For example, if utilities are associated with outcomes, each of several outcomes may be assigned a numeric value of utility, with higher numbers representing more preferred outcomes. Utilities may be based on the patient's actual and/or projected health (optionally including side effects); an assessment of a state of the disease such as the disease' level of virulence, level of contagiousness, or how easily attackable the disease is in its current state (e.g., by a drug or drug regimen); how likely the disease is to evolve from the current state to malicious states; and/or the current and/or expected future cost of treatment and/or other costs to the treater, patient or third party payor. The treater's utility for any outcome, intermediate state or transition in the game may also include, for example, a measurement of utility that considers the patient mortality rate and/or financial costs of treatment associated with the item.

In an embodiment, one or more actions may be associated with one or more parameters. A parameter may be a feature or characteristic of an action. Example parameters may include, without limitation, a duration of an action, a type of regimen to which the action pertains such as for example, a dosage regimen, an exercise regimen, a dietary regimen or guidelines and/or the like.

By way of example, a system may use various sensors to measure cytokines via a blood test such as an enzyme-linked immunosorbent assay, a dermal tattoo sensor, or other assay that can detect cytokines in a patient's blood. Cytokines are regulators of immunity, and certain cytokines can be useful in cancer immunotherapy. Outputs from a test that measures levels of different cytokines can be entered into systems described in this document and the plan computed by the system can prescribe different next treatments for different measured vectors of cytokine concentrations, such as using an infusion pump to insert any of various small-molecule treatments or chemotherapy treatments into the patient's blood stream.

In some embodiments, the system can be used to model various possible treatment plans that include various medicines in a pill that a patient swallows, which releases different medicines based on the environment inside the patient that the parts of the pill face. This can be made, for example, using a DNA cage where one places the treatment inside the cage, and the cage opens automatically under certain environmental conditions. Different DNA cages open under different environmental conditions so different treatments can be released in different environmental conditions. Descriptions of those DNA cages and descriptions of the alternative treatments can be entered into systems described in this document. The system then models cage-treatment pairs as possible moves for the treater in the game. The system outputs which cages are to be used in what quantities, and what treatments are to be included in which cages in which quantities.

The output of the model may be a plan for treatment. In game theory, a plan is often called a "strategy." In some scenarios, the output may include one or more contingent plans. Contingent plans are sometimes known as online control policies, in that they prescribe different actions based on the results of observations. Unlike single-shot games, we consider sequential games where a player's strategy may include a sequence of actions. Even more generally here, a player's strategy can be a contingent plan, that is, his probability distribution over next actions to take may depend on his observations about how the game has played out so far (and any private information and beliefs he may have). A full contingent plan may be generated in advance before treatment begins, or the planning may be done incrementally by interleaving planning and execution.

One way of tackling the game model is opponent exploitation (e.g., where the opponent is the disease) beyond what any equilibrium strategy can accomplish. It was folk wisdom in game theory that one cannot exploit an opponent safely (that is, without exposing oneself to exploitation, or risking doing worse than an equilibrium strategy in expectation) beyond what the best equilibrium strategy can accomplish. However, in the system described in this document, one accepts that safe opponent exploitation is possible.

A plan can serve as a treatment plan that is implemented in a patient, or it can serve as a recommendation for a party such as a doctor who makes the final decision. The system may, in some embodiments, produce two or more alternative solutions for the medical professional and/or patient to select among. For example, the system may propose a less radical treatment plan with a light drug cocktail that may have a shorter life expectancy but a higher quality of life than an alternative, more aggressive drug cocktail with a longer life expectancy.

Applying the system at a molecular level may involve developing a treatment for generic patients or for a limited set of prototypical patients. The actions of the treater at any point in the game may include what drug or drug cocktail to use, an amount of the drug or drug cocktail that should be used and/or the like. The actions may include choosing a cocktail of existing drugs. The actions can also include de novo drug designs, for example, the actions can include new molecules. This is one way how the present invention can be used for drug design since the output of the system will include a plan that may include one or more de novo drugs. The actions can also include conducting tests on the patient and/or the virus population in the patient, and/or the like.

The actions of the disease at any point in the model may include the most likely mutations and the most likely mutating locations or binding sites. A model may be used to predict how well one or more of the treater's actions addresses one or more of the disease's actions. For example, if a treater's action is to prescribe a drug cocktail, a model may be used to predict how well each of the drugs in the cocktail would bind to each mutation at each binding site.

The output of the model may be a plan of treatment over a period of time that may include one or more contingencies.

For example, applying the system at a population level may involve developing or identifying an appropriate course of treatment for a population of patients or potential patients. For example, applying the system at a population level may involve developing a course of treatment for a biological outbreak such as an influenza or other epidemic, or even for a wider ranging epidemic that is considered to be a pandemic such as a coronavirus pandemic. The actions of the disease at any point in the game model may include spread of the influenza or other virus strands (possibly including mutations) to different parts of the population. This is unlike the current way of treating influenza in the United States, where a single vaccine is developed per year for the entire flu season, and the choice is merely whether or not to vaccinate a person. At any point in the game model, the actions the treater may take may include, without limitation, determining a drug or drug cocktail to use in one or more parts of a population, or determining whether one or more parts of the population should be hospitalized, quarantined, and/or the like. The treater's possible actions may also include the selection from a potentially unrestricted space of de novo molecules (so that drug design can be incorporated within the population-level game). The treater's actions may also include conducting tests on patients from various subsets of the population, and or testing one or more aspects of the virus within the patients. The treater's utility could be based on, for example, a mortality rate or one or more costs such as hospitalization costs.

In an embodiment, the output of the model may be a treatment plan over a period of time. The plan may detail how the treater changes the treatment or testing over time in each portion or segment of the population. The plan also may have contingencies at various points, where the next step in the plan after that point will depend on certain parameters, such as test results.

While the example described above applies the system at the population level, it is possible that various additional levels can be used. For example, when battling a disease at the population level, the system could also oppose the disease at the molecular level. Such an embodiment could be helpful if the virus is new so there is little experience in how it behaves in the population.

Figure 1:
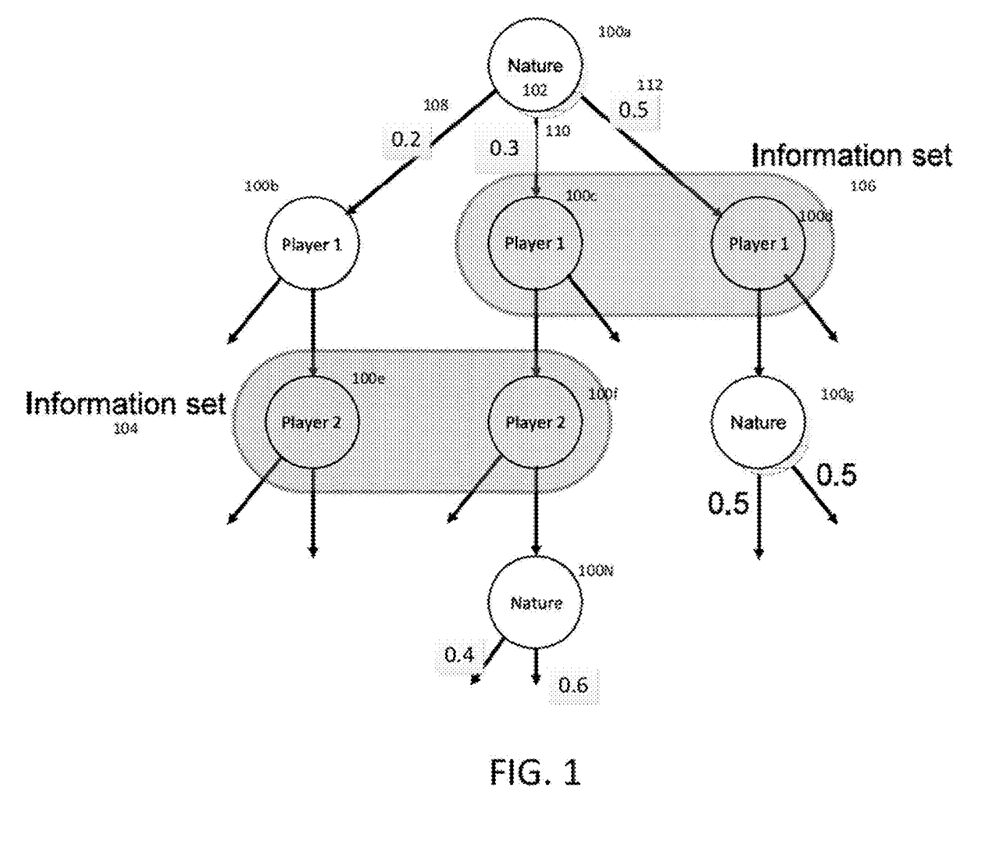
FIG. 1 is an example representation of an incomplete-information game according to an embodiment.

FIG. 1 illustrates an example representation of an incomplete-information game according to an embodiment, and the discussion below will describe how a game may be solved. As illustrated by FIG. 1, each node 100a-N represents the player whose turn it is to move. FIG. 1 illustrates a two-player, zero sum game. However it is understood that additional players may participate in the game, and that the game may not be a zero sum game.

In an embodiment, uncertainty in the game may be represented in FIG. 1 by a player referred to as "Nature." A Nature player 102 may make moves based on fixed probabilities rather than strategic moves. For example, as illustrated by FIG. 1, there may be a 30% chance that Nature player 102 makes move 108, a 50% chance that Nature player makes move 110 and a 20% chance that Nature player makes move 112.

Incomplete information is represented in FIG. 1 by information sets 104, 106. In an embodiment, an information set is a collection of one or more nodes in a game tree such that the player whose turn it is to move at the information set does not know which node of the information set is the actual game state at that point.

The game model may also include taking actions over time, where there is no pre-specified order in which the players are supposed to move. The actions of the players may also include doing some action for a specified period of time or at a specified point in time. For example, the treater's actions may include applying a specific drug cocktail starting at a certain time and ending at another time.

Other representations of the game can also be used. Other general game representations can be used, such as, without limitation, the normal form (aka strategic form aka matrix form), sequence form, graphical game, and action-graph game. Other compact or application-specific game representations can also be used.

By way of another example, an extensive-form game may be used and represented as a tuple (N, A, S, $\mathcal{H}$, $\sigma_0$, u, $\mathfrak{T}$) in which N is the set of players. A is the set of all actions in the game. S is a set of nodes corresponding to sequences of actions. They describe a tree with root node $s^r \in S$. At each node s, it is the turn of some Player i to move. Player i chooses among actions $A_s$, and each branch at s denotes a different choice in $A_s$. Let $t^s_a$ be the node transitioned to by taking action $a \in A_s$ at node s. The set of all nodes where Player i is active is called $S_i$. $Z \subset S$ is the set of leaf nodes. The utility function of Player i is $u_i$: $Z \to R$, where $u_i(z)$ is the utility to Player i when reaching node z. $Z_s$ is the subset of leaf nodes reachable from a node s. $\mathcal{H}_i \subseteq \mathcal{H}$ is the set of heights in the game tree where Player i acts. Certain nodes correspond to stochastic outcomes with a fixed probability distribution. Rather than treat those specially, we let Nature be a static player acting at those nodes. $\mathcal{H}_0$ is the set of heights where Nature acts. $\sigma_0$ specifies the probability distribution for Nature, with $\sigma_0(s, a)$ denoting the probability of Nature choosing outcome a at node s. Imperfect information is represented in the game model using information sets. $\mathfrak{T}_i \subseteq \mathfrak{T}$ is the set of information sets where Player i acts. $\mathfrak{T}_i$ partitions $S_i$. For nodes $s_1$, $s_2 \in I$, $I \in \mathfrak{T}_1$, Player i cannot distinguish among them, and so $A_{s1} = A_{s2} = AI$.

We denote by $\sigma_i$: $S_i \to [0, 1]$ a behavioral strategy for Player i. For each information set $I \in \mathfrak{T}_i$, it assigns a probability distribution over $A_I$, the actions at the information set. $\sigma_i(I, a)$ is the probability of playing action a at information set I. A strategy profile $\sigma = (\sigma_0, \ldots, \sigma_n)$ consists of a behavioral strategy for each player. We will often use $\sigma(I, a)$ to mean $\sigma_i(I, a)$, since the information set specifies which Player$_i$ is active. As described above, randomness external to the players is captured by the Nature outcomes $\sigma_0$.

In an embodiment, solving a game model, such as that illustrated in FIG. 1, may result in a treatment plan. In an embodiment, solving a game model may involve one or more solution concepts. A solution concept may be one or more rules for predicting how a game will be played.

Example types of game theory solution concepts include, without limitation, Nash equilibrium, subgame perfect equilibrium, perfect Bayesian equilibrium, sequential equilibrium, trembling-hand perfect equilibrium, extensive-form perfect equilibrium, extensive-form proper equilibrium, admissible strategies, normal form perfect equilibrium, quasi-perfect equilibrium, normal form proper equilibrium, and correlated equilibrium. Approximate versions of any of the foregoing may be used within the scope of this disclosure.

In an embodiment, if a game model has more than two players, then solution concepts having to do with coalitions, such as, for example, strong Nash equilibrium, coalition-proof Nash equilibrium, strong correlated equilibrium and other variations may be used.

In an embodiment, if a game is modeled as a non-cooperative game, the solution concept may define which strategy profile and beliefs (e.g., probability distributions over nodes within each information set) constitute solutions to the game. In other words, a solution concept may identify one or more strategy profiles that are reasonable solutions for "rational" players to use.

In an embodiment, a strategy profile may include one strategy for each player. Each player's pure strategy may be a contingent plan that selects an action (or deliberate inaction) based on what has transpired in the game so far, such as for example, the path of play by all the players and Nature and the time that has elapsed. Typically a player cannot condition her action on actions from the past that she has not observed. Therefore, typically each player has to decide his/her action based on the information set. So, a pure strategy for a player may prescribe one action per information set, for those information sets where it is that player's turn to move, although other variations are possible.

In an embodiment, a player's mixed strategy may be the player's probability distribution over the player's pure strategies. In an embodiment, behavioral strategies that assign probability distributions to actions at each information set may be used. In these ways, a player may act with randomization.

The information sets in a model may include data that describes possible actions of a disease and/or treater. Such data can be provided by any suitable source, such as medical and/or scientific literature, from input by a treater and/or patient, from results databases, disease evolution models, clinical trial results, and so on.

In some embodiments, the Nature player may play a role in the game by introducing stochasticity. For example, nature can introduce stochasticity in the patient's state and in test results (probability of each reading conditional on the true state). The moves that nature can make (and the probability distribution over those moves) for points in the game where it is nature's turn to move can be generated from scientific papers or databases of results, disease evolution models and simulations, tests on humans or animals, past experience about the disease on a particular patient of segment of patients, experience gathered about the disease while using the system, active learning, available data on the probabilistic errors that given tests have, and so on. The learning and information extraction and/or information fusion can be done using machine learning techniques or manual approaches.

In some embodiments, the moves that the treater can make, as contained in any given information set for the treater, may include standard treatments for the condition, and/or new potential treatments that the treater wants the game-solving system to consider as possible parts of the treatment plan that the system outputs. The standard treatments can come from any suitable source such as guidelines, common practice, scientific papers or databases, and so on.

In an embodiment, in some situations, a game-theoretic approach may be too conservative. For example, a game-theoretic approach may be too conservative in settings where it is known or believed that that the opponent will not behave in the worst possible way. In these situations, opponent modeling and opponent exploitation may be used.

In an embodiment, an opponent model may predict what an opponent would do in various information sets. An opponent model may be generated from result sets, disease evolution models and simulations, experiments, trials that test treatments and/or contingency plans for treatment, past experience about an opponent, experience learned about an opponent while using the system, active learning and/or the like. In the example of HIV, an opponent model may be generated based on data describing which antivirals tend to cause specific mutations in reverse transcriptase, protease or integrase (e.g., in the form of a probability table), and/or data on efficacy of other antivirals against such mutants. Thus, the system may also develop and/or update the opponent model based on information learned while playing the game (e.g., executing the treater's plan together with the opponent's strategy and nature's strategy—in the physical world or in simulation). The opponent model can be generated automatically using a host of different possible algorithms and/or using manual approaches.

There are many ways of using learning (automated and/or manual) to construct and/or refine the opponent model and the model about the nature player and the game itself (e.g., the game's structure and the utilities in the game). For example, on the simple end, if one observes the opponent or nature taking an action that is not in the model, one can add that action to the model. Also on the simple end, as one observes an action by the opponent or by nature, one can update the counter for that action for that state of the game (of course, one may have to aggregate this information across states that one cannot distinguish among, for example, due to incomplete information). Then, one can use the counter-based action frequencies at that state as the model of how the opponent or nature is likely to behave at that point of the game. There are many further possible improvements to the learning. For example, one can use machine learning techniques to conduct generalization of the leanings across states. As another example, one can assume first that the opponent behaves rationally according to game theory, and then start adjusting the opponent model toward observed behavior of the opponent as we get more knowledge about the opponent's actual behavior based on observations or from new scientific knowledge from books, papers, or databases.

An opponent model can also combine frequentist approaches (such as the ones described in the previous paragraph) with assumptions about the opponent's ability to conduct only limited lookahead (such as the approaches described earlier in this document).

In an embodiment, a player may start by playing game-theoretically and then adjust play toward exploiting an opponent as a more robust opponent model is developed over time based on experience. An example algorithm that may be applied to this approach is described in, for example, "Game theory-based opponent modeling in large imperfect-information games," by Sam Ganzfried and Tuomas Sandholm, published in International Conference on Autonomous Agents and Multi-Agent Systems, AAMAS, 2011.

In an embodiment, the system may identify an $\epsilon$-safe best response, or approximation thereof. An $\epsilon$-safe best response is one that will do at most a predefined $\epsilon$ worse (in terms of utility) than a game-theoretic strategy. This strategy may exploit a model of the opponent maximally, subject to the constraint that even against the worst-case opponent, it will do at most $\epsilon$ worse than a game-theoretic strategy. Typically, although not necessarily, the $\epsilon$ in the $\epsilon$-safe best response is measured in terms of an expectation over all the players' (including nature's) possibly randomized strategies. One other way to measure $\epsilon$ is to take an expectation over some (or none) of the players, considering the worst case of the other players' strategies.

In an embodiment, the system computes an exploitative (e.g., in the sense of exploiting the opponent more than any game-theoretic equilibrium strategy can) strategy that is safe, that is, no worse than a game-theoretically optimal strategy. This is possible if the opponent makes mistakes, i.e., plays worse than a fully rational game-theoretic player would. In zero-sum game settings, the utility (measured typically, but not necessarily, as an expectation over the players' and nature's randomized strategies) that the disease foregoes by making a mistake is a gift to us as the treater. In this context, the sum of the gifts that the opponent has given the player (minus any gifts that the opponent may have received from the other player) may be represented by $\epsilon$. Then, the system can use an &safe best response and still be absolutely safe. However, one may wish to separate out the gifts (which are due to the opponent's mistakes) from luck (i.e., lucky draws of the randomizations). One aspect of this fully safe opponent exploitation technique is that it does not require one to be able to compute the sum of the gifts exactly: a lower bound suffices to guarantee safety. This also means that it is possible to use the technique even if one is not sure that one's game model is exactly accurate.

In an embodiment, a set of strategies may be computed. It may then be determined which strategy performs best against an opponent based on simulated or real world learning. In an embodiment, no-regret learning algorithms may be used to perform well not only in the end but also throughout the learning process.

In an embodiment, a best-response strategy to an opponent model (and the model of nature if the nature player is part of the game), or an approximation thereof, may be used. A best-response strategy may be one that produces highest utility for a player, given the other players' (including nature's) strategies (typically measured in expectation, but one can also measure it in terms of worst case or other measures, for example, one can make worst-case assumptions about some of the other players strategies (possibly only at some points of the game, e.g., ones where we do not have much knowledge about the opponent's behavior) and/or nature's actions (possibly only at some points of the game, e.g., ones where we do not have much knowledge about nature's action probabilities)). To find one or more such solutions or approximations thereof, techniques from stochastic programming (sometimes also called dynamic optimization and sometimes also called stochastic optimization) may be leveraged. The stochastic programming techniques applicable here include both exact and approximate approaches. The stochastic programming techniques applicable here include both offline stochastic programming techniques where the plan is generated up front before starting to execute it, and online stochastic programming approaches where the plan is generated in pieces (typically one action at a time)—interleaving planning and execution. Example algorithms that may be applied in this setting may include, without limitation, sample trajectory-based optimization techniques and policy gradient algorithms.

In sample trajectory-based algorithms, possible paths of the future (in the game model in this context) are drawn. These are called sample trajectories or scenarios. Then a plan is computed that does well (typically in the sense of utilities weighted by probabilities, but other measures such as more risk averse ones can also be used) across many of those sample trajectories. There are various algorithms for doing this computation. Some of them consider all of the scenarios simultaneously. Others make a tentative plan for each scenario separately and then use various methods for aggregating those plans into an overall plan.

In policy gradient methods, the plan is parameterized by a (typically relatively small) number of parameters that control what the plan does. Thereby the computation to determine a plan is simplified to a computation that tries to optimize (approximately or exactly) the parameters.

In another embodiment, one can use a hybrid of solving the game model using a game-theoretic solution concept and solving it using opponent modeling/exploitation. For instance, one can assume that the opponent plays according to the opponent model in points of the game where one has a significant amount of statistical information about the probability distribution over the actions that the opponent takes at that point, and assume that the opponent plays game theoretically at other points of the game.

In another embodiment, if the strategy that is computed for the treater is randomized, the amount of randomization is decreased before the strategy is output or before it goes into implementation. The reduction can be done, for example, by rounding the probabilities that are less than some threshold to zero, and scaling up the other probabilities at that information set up accordingly so they sum up to one. As an extreme case, one can simply use the highest probability action/strategy. Such reductions of randomization have been found helpful even in some poker strategies, but in the context of this document, reduction of randomization may be particularly useful because the opponent is not rational or deliberative. So, there is less need to worry that one's actions signal too much about one's private information to the opponent, which is typically the main motivation for randomization in games.

Figure 2:
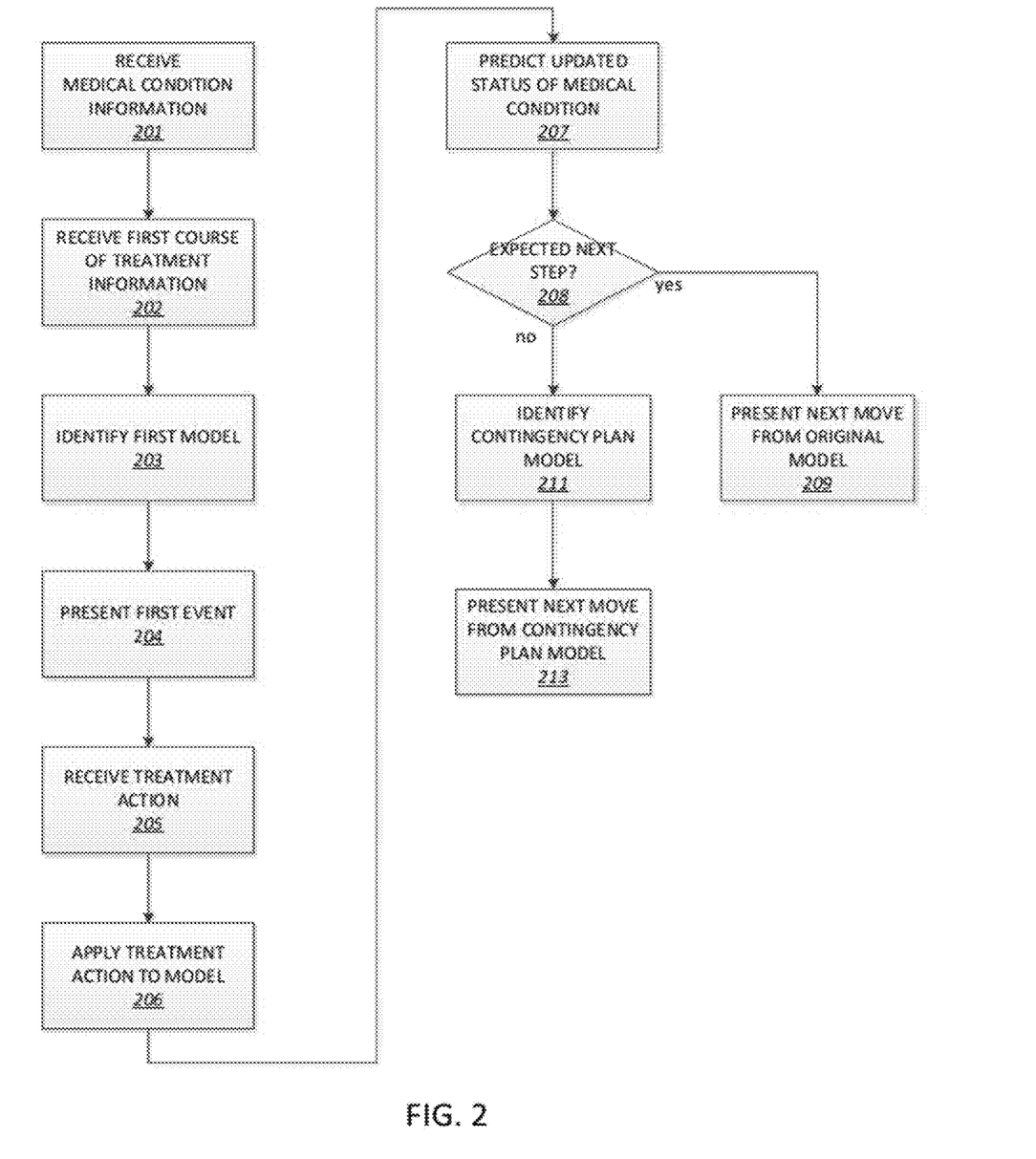
FIG. 2 is a flow diagram that illustrates an example process for medical treatment planning using a sequential game.

FIG. 2 illustrates an example of a process flow that a medical treatment or drug design planning system may implement. To develop a course of treatment for a medical condition, which may include the design and/or administration of one or more drugs or drug regimens, exercise regimens, other therapies and the like, a computer-implemented system may present a user interface that implements a model as a sequential game that receives input from a treater. Alternatively, the system may implement the game automatically with a virtual treater and produce a recommended course of treatment or drug design as an output.

The system may identify a description of a game by receiving information corresponding to the medical condition (step 201). The system may receive this information via a user interface or communications port from a doctor, patient, researcher or other individual or system having information about the medical condition. The system also may receive, via the user interface or a communications port, one or more possible treatment actions for the medical condition (step 202). The possible treatment actions also may include a sequence for the actions, and one or more parameters for each action The system will also receive one or more possible medical condition actions that a disease or other medical condition may take (step 203) in response to a treatment action or other input or influence.

After receiving the treatment actions and medical condition actions, the system may implement programming instructions to develop a first model for a sequential game (step 204). The system may do this by accessing a data storage facility, identifying an appropriate model for the course of treatment and retrieving the identified model. Alternatively, it may build a new model. For example, the model may include possible medical condition actions such as the medical condition mutating in one or more ways, evolving in one or more ways, and/or the like. Treatment actions in the model may include applying one or more treatments, taking one or more measurements, taking no action and/or the like.

In an embodiment, one or more possible actions that a medical condition and/or a treater may take may be based on one or more considerations. A consideration may be a state, status or other condition of a patient, a medical condition, a treatment and/or the like. Example considerations may include, without limitation, a current status of a patient's health, a projected health of a patient, how virulent a medical condition is, how contagious a medical condition is, how easily attackable or treatable a medical condition is in its current state, a cost of treatment, a projected future cost of treatment, other costs and/or the like.

The model also may include an information set associated with the treater, an information set associated with the medical condition, or both. The information set for either player may include one or more actions that the player could take based on any suitable parameters such as medical condition state, previous actions taken, time elapsed, or other parameters.

In an embodiment, the system may select medical condition actions and/or treater actions based on user input, based on commands received by the system from another system, by implementing rules or other functions of a model, or via automatic or random selections by implementing programming instructions and/or the like. The model represents implementation of the set of actions in accordance with the sequence and the parameters.

To solve the model (step 205), the system may apply a game-solving algorithm to a model with one or more utilities. Any medical condition action may be responsive to an immediately-received treatment action (and ones that were prior, but not immediately prior), or vice versa. After each treatment action, the model may include information that the system uses to predict an updated status of the medical condition based on the application of the treatment action to the medical condition). Predicting the updated status may include determining an expected patient response to the treatment action. Because the model may include one or more contingent plans, any medical condition action and/or treatment action may be depending on one or more parameters, such as the previous action taken by the other player and/or parameters from an information set. Also, as described above, when solving the model a treatment strategy may include the setting of a trap that may lure the medical condition into a state in which the condition may be more easily treated, less virulent, less contagious, or otherwise in a more preferable state for the patient and/or others. Suitable methods of solving may include opponent modeling techniques, opponent exploitation techniques, or techniques for solving according to game theory solution concepts such as those described above.

The system may present an output as a treatment plan (step 206) (i.e., the treater's strategy, which may be a contingent plan) that includes the set of medical condition actions and treatment actions. The treatment plan may include the actions, the traps, dosage regimen implementation, medical treatment planning, and/or other information that led to the result.

Although the description of game play described above used the example of application of treatment actions on an individual level, as noted above the actions and game play also may occur at a molecular level (such as would be the case where the "treatment plan" includes a design for a new drug), or at a population level.

The goal of the game may be to identify what treatment plan (i.e., strategy) is expected to result in a state in which the medical condition may be more easily treated, a state in which the medical condition is less virulent, or a state in which the medical condition is less contagious. The system may prepare and output a report of these treatment actions or the complete treatment plan for implementation by a treater in real life, outside of the game.

Figure 3:
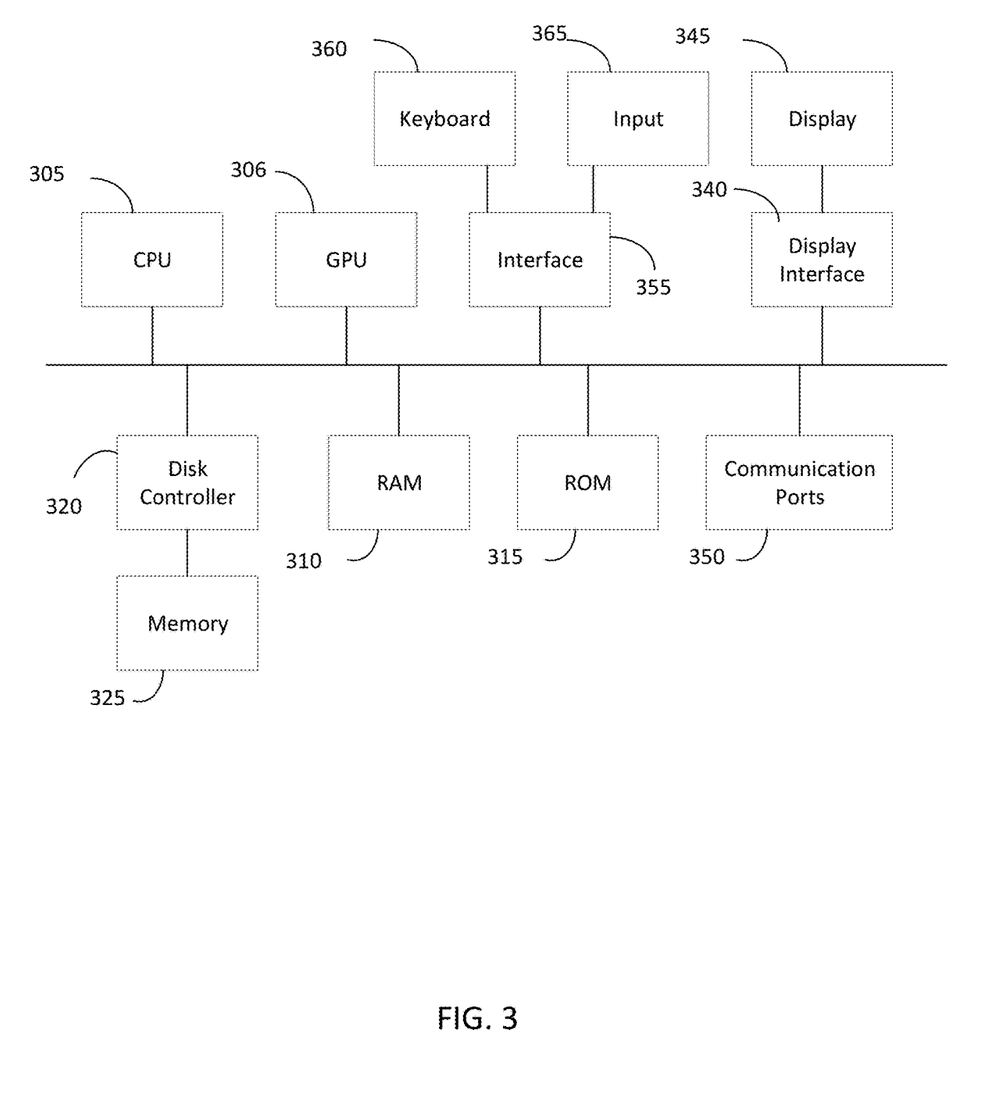
FIG. 3 is a block diagram illustrating various elements of an example of a computing device.

FIG. 3 depicts a block diagram of an example of internal hardware that may be used to contain or implement program instructions, such as the process steps discussed above, according to embodiments. A bus 300 serves as an information highway interconnecting the other illustrated components of the hardware. CPU 305 represents one or more processors of the system, performing calculations and logic operations required to execute a program. CPU 305, alone or in conjunction with one or more of the other elements disclosed in FIG. 3, is an example of a processing device, computing device or processor as such terms are used within this disclosure. In addition to CPU 305, the system may include a graphics processing unit (GPU) 306, which is a processor designed to render two-dimensional and three-dimensional graphics on a display device. Read only memory (ROM) 310 and random access memory (RAM) 315 constitute examples of memory devices or processor-readable storage media.

The computation of a strategy for the treater in a game with a large state space would typically be prohibitively slow using just a CPU. For example, a relatively simple course of treatment may include monitoring a patient's blood sugar levels and using the monitored information to decide when the patient should receive a dose of insulin, and at what level. This is a relatively simple level involving two variables, the measured blood sugar level and the quantity of insulin inserted. However, other treatment decisions involve dozens or hundreds of possible variables, each of which may have values that may change as treatment progresses. For example, consider the goal of determining a course of treatment for a cancer patient. Planning the course of treatment may involve identifying which of a patient's T cells to use in a course of CAR T-cell therapy, and how the T cells should be modified to produce chimeric antigen receptors on their surface. Such a course of treatment involves many variables, and the values selected may change over time depending on how the patient's medical condition reacts to the treatments. Such treatment decisions benefit from the approaches described in this document, as the strategies can be computed with many more options that are impossible for a human mind to handle.

To enable computation of strategies in practice, special hardware is needed, such as graphics processing units (GPUs), field-programmable gate arrays (FPGAs), or application-specific integrated circuits (ASICs). This special hardware is typically placed inside a supercomputer or cluster of computers, but for medium-sized games it may suffice to have it attached to a single regular computer.

For example, a GPU is typically a multi-core processing device that is capable of performing thousands of operations at once in a parallel processing environment. Some GPUs may include tensor cores, which represent variables and results of a mathematical operation by an array so that the GPU can perform multiple operations per cycle. For example, in a GPU core that represents variables in a 4×4 array, the system may perform 64 (4×4×4) instances of the A×B+C=D equation per cycle. If the GPU has 8 cores, it could perform 512 instances of the function per cycle. By directing the game solving algorithm to a GPU, the system can improve operation of the system and provide a result more quickly than a standard computing device. In a computing device having both a CPU and a GPU, the system may perform compute-intensive parts of the game solving algorithm on the GPU while continuing to perform other parts of the algorithm and functions, such as receiving and processing user inputs for the game solving algorithm, via the CPU. Unlike a CPU, implementation of the algorithm on a GPU allows for a system having a large state space. When the game state space is large, it is not possible to store even one variable for each state (in memory or on any other storage device). This becomes prohibitive already at around $10^{15}$ states, and treatment planning games will typically have significantly more states than that. Even two-player no-limit Texas hold'em poker (with 200-big-blind stacks) has $10^{161}$ states, and biological games will typically be larger than that. To deal with a large state space, a neural network (also known as deep learning) (or other machine learning method, e.g., other supervised learning method) can be used to generalize across states, so the system can offer a seemingly stored value for each state while actually only storing weights of a neural network, which is a dramatically smaller collection of variables. One with ordinary skill in the art will appreciate that neural networks can do such generalization across states. One with ordinary skill in the art of artificial intelligence will also appreciate that the issue is not just storage but also the neural network generalization will allow the game-solving algorithms to not have to visit all states (which would be impossible in large state spaces) but to generalize the plan to unvisited states and thereby compute strong game strategies while visiting only a miniscule fraction of the states. For both of these reasons, neural networks play an enabling role in scaling to large state spaces. Neural networks run many orders of magnitude faster on a GPU than on a CPU, and thus they cannot be used for large problems in practical time on a CPU, but can on a GPU.

As an example in our treatment planning context, when counterfactual regret minimization is used in equilibrium finding, the neural network can be used to store counterfactual regret values for states (information sets) of the game and/or action probabilities for states of the game.

As another example in our treatment planning context, when opponent exploitation is used, the neural network can be used to store values for states (information sets) of the game and/or action probabilities for states of the game.

As yet another example in our treatment planning context, when exploitation of limited lookahead is used, the neural network can be used to store evaluation function values at the leaves at the end of the lookahead depth, values for states of the game, and/or action probabilities for states of the game.

As a different way of using a GPU in our treatment planning context, one can use a GPU to have the algorithm explore multiple branches of the tree simultaneously, that is, in parallel.

As mentioned above, an FPGA or ASIC can be used to accelerate the computation compared to a CPU, so as to enable treatment computation in large state spaces. They can be used to increase parallelism of the branches explored and/or to support generalization across states (e.g., by running neural networks or other machine learning algorithms (supervised learning algorithms)).

A controller 320 interfaces with one or more optional tangible, computer-readable memory devices 325 to the system bus 300. These memory devices 325 may include, for example, an external or internal disk drive, a hard drive, flash memory, a USB drive or the like. As indicated previously, these various drives and controllers are optional devices.

Program instructions, software or interactive modules for providing the interface and performing any querying or analysis associated with one or more data sets may be stored in the ROM 310 and/or the RAM 315. Optionally, the program instructions may be stored on a tangible computer readable medium such as a compact disk, a digital disk, flash memory, a memory card, a USB drive, an optical disc storage medium, such as a Blu-ray™ disc, and/or other recording medium.

An optional display interface 340 may permit information from the bus 300 to be displayed on the display 345 in audio, visual, graphic or alphanumeric format. Communication with external devices, such as a printing device, may occur using various communication ports 350. A communication port 350 may be attached to a communications network, such as the Internet or an intranet.

The hardware may also include an interface 355 which allows for receipt of data from input devices such as a keyboard 360 or other input device 365 such as a mouse, a joystick, a touch screen, a remote control, a pointing device, a video input device and/or an audio input device.

Figure 4:
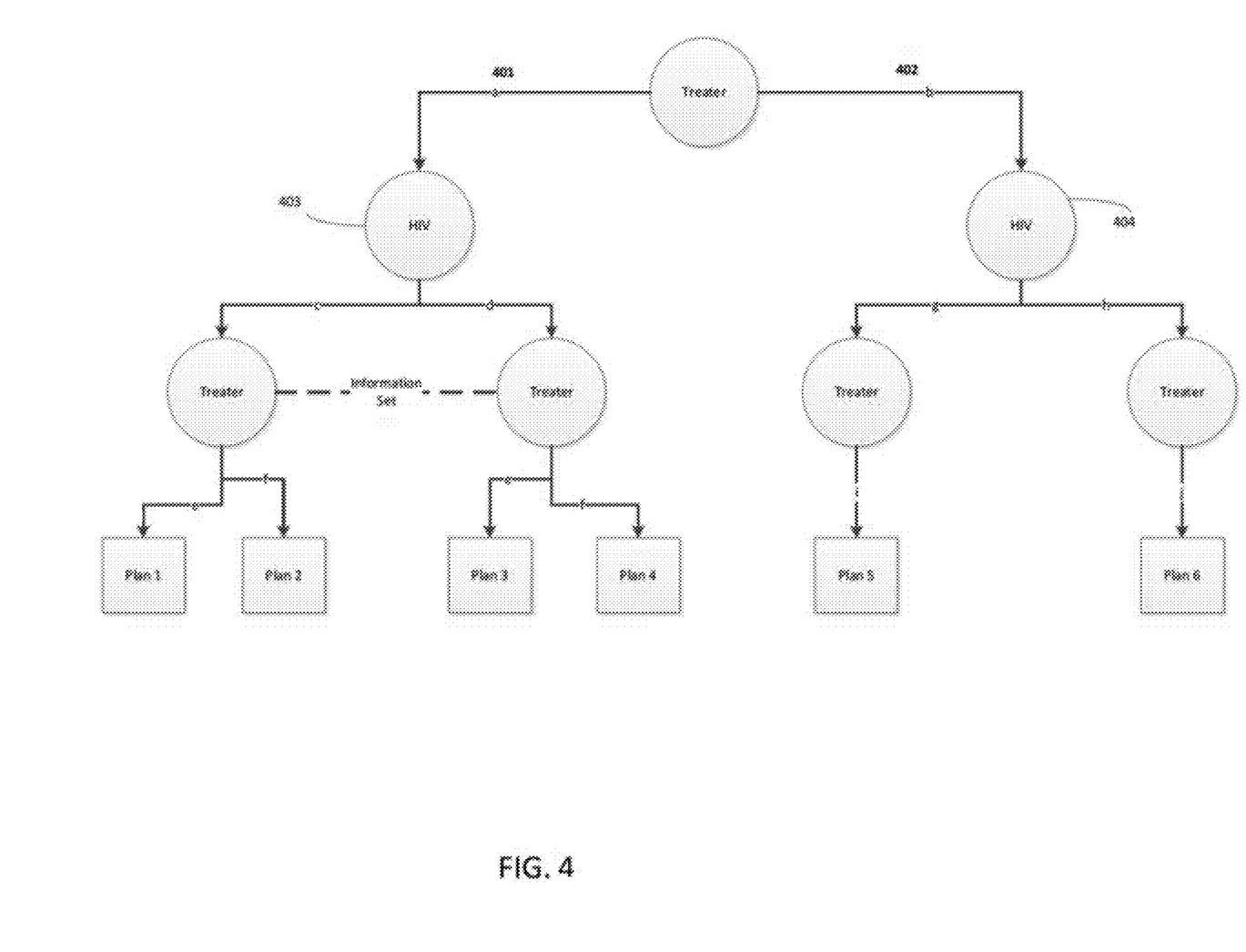
FIG. 4 is a tree diagram illustrating an example of game play in the context of treating a disease such as HIV.

FIG. 4 illustrates an example of sequential game play, using a tree-like structure of moves. In this example, the system may be used to identify and/or develop a drug and/or drug cocktail for a patient or set of patients who are HIV-positive. The actions of the disease (HIV) at any point in the game model may include, for example, mutation, and the model may include the most likely mutations in the most likely mutating locations (binding sites) of HIV-1 Protease. The disease may take action by selecting and implementing a mutation, or by selecting no mutation. The system may select any of these mutations as an action for the disease during game play.

The actions of the treater at any point in the game model may include selecting a pharmaceutical regimen to prescribe to the patient. The selected pharmaceuticals may be existing drugs and/or drugs designed and/or suggested by the system. Any number of pharmaceutical regimens may be identified and/or selected. The actions of the treater also may include conducting one or more tests on the patient and/or the virus population in the patient. At any decision point, the treater may be able to choose from one of a set of actions, each of which will lead to one or more possible actions by the disease, in a tree-like arrangement such as that illustrated in FIG. 4.

For example, when presented with an HIV-positive patient, the system may give the treater the choice of selecting a first course of treatment 401-*a* corresponding to a first drug cocktail, or a second course of treatment 402-*b* corresponding to a different drug cocktail. Each action may result in a different result state 403, 404 for the disease. Next, the disease may make a move. For example, starting from result state 403, the disease may experience a mutation 405-*c* that worsens the condition of the patient, or it may remain static or go into remission 406-*d* so that the patient's condition improves. Based on the disease's action, the treater may then select from a set of available next actions 407-*e*, 408-*f* in the information set, and so on.

The system may apply a model to predict how well each of the treater actions (i.e., drugs) may address the disease actions (e.g., by binding to each mutation at each site). Any now or hereafter known model may be used, such as those disclosed by: (1) Kamichetty, "Structured Probabilistic Models of Proteins across Spatial and Fitness Landscapes" at pp. 121-127 (Carnegie Mellon University, March 2011); or (2) International Patent Application No. PCT, US2012/026966, filed Feb. 28, 2012, titled "Using game theory in identifying compounds that bind to targets." The utilities of the players may, for example, be associated with predicted binding energies at the sites. For example, it may be the sum across the sites. In some embodiments, the treater's utility may be the that sum but with a negative sign because the treater may want to minimize that sum. The output can be a plan over time, that is, how the treater changes the treatment over time. The plan can include comprises a set of possible treatment actions and possible medical condition actions, at least some of which are included in information sets along with a probability distribution for each such action. The output plan can also include one or more contingent plans where the rest of the plan depends on the results of tests.

In some embodiments, game play may occur over multiple paths of the same tree. This may occur, for example, if multiple strands of a virus experience different mutations. Thus, in the context of FIG. 4, game play may occur, for example, along each of the two primary trunks of the tree. The state of the disease at any given point could include all configurations in which the virus is currently modeled to exist in the host.

Systems such as those discussed in this documents may provide various benefits. For example, the algorithms can solve game models better than humans can (and in many cases optimally), so there is a potential to generate better treatment plans than doctors and policy committees generate today. In fact, present day manual medical treatment planning is rather ad hoc and unsophisticated from the perspective of the state of the art in game solving algorithms—in particular in the ability to generate high-quality sequential plans. In addition, because the planning is automated, it may be dramatically faster and may require fewer human resources. This means that custom plans can be generated for more specific population segments and even for individual patients. The speed also may enable a user of the system to conduct what-if analyses (sensitivity analysis) to test how the system-generated plan would change under different assumptions about Nature's moves (impact of treatments on patient, accuracy of tests, etc.). This has the potential to also guide where future medical research should be conducted: the most valuable knowledge to generate is the knowledge that will impact the treatment plans.

The description so far has discussed a game model where the disease may have a complex (e.g., high-dimensional) state, but whenever it is the disease's turn to move, it can select only one move. In other words, the disease proceeds down a single path. However, embodiments of the system also include variations where the disease may have a simpler state, but it may be able to proceed down any of multiple paths of a decision tree. This is because the mutation or other progress of a disease can proceed down multiple paths simultaneously, e.g., a human can have multiple strands of a virus simultaneously. The disease has no strategic plan for evolution, but the treater has an advantage of looking ahead and developing contingency plans based on various mutations or evolutionary steps of the disease. The system described in this document may allow the treater to assess multiple courses of action by simultaneously playing multiple paths within the game. In addition, the treater may place one or more traps for the disease. Again, a model can be used to determine whether the traps are likely to lure the disease.

Although there have been prior attempts to use game theory for drug design, those game models have been single-shot games, that is, each player (typically in parallel) chooses one action from a set of actions. The system described in this document uses sequential game models, and it introduces the options of contingent plans, traps, and opponent exploitation, thus providing many more options for the path of play and for game solving than a single-shot game (or a single-shot game analysis of endpoints of a simulation). Also, in the sequential context, the system may capture and predict the effect of information-gathering actions (such as measuring various parameters of the disease or the patient) and employ game-theoretic screening devices. No prior system has employed a model where a treater is an actual player—and treatment actions that the treater may take are used—in the game.

The above-disclosed features and functions, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

The invention claimed is:

1. A system for developing a course of treatment for a medical condition, comprising:
   a central processing unit (CPU);
   a graphics processing unit (GPU);
   a user interface;
   a communication port; and
   a non-transitory, computer-readable memory comprising one or more programming instructions that, when executed, will cause one or more of the processors to, upon receiving, via the user interface or the communication port, information corresponding to a medical condition:
      identify a set of possible treatment actions that a treater can take to treat the medical condition, and a plurality of sequences for the actions,
      identify a model, wherein:
         the model comprises an opponent model, and in which the medical condition is considered to be an opponent to the treater; and
         the model includes a plurality of possible medical condition actions hat represent possible responses of the medical condition to one or more of the possible treatment actions,
      solve the model to generate a treatment plan for the medical condition, where the treatment plan comprises a set of the possible treatment actions, and
      output a report of the treatment plan,
   wherein:
      the instructions to identify the possible treatment actions and the model are, when executed, implemented by the CPU;
      at least some of the instructions to solve the model are, when executed, implemented by the GPU; and
      the one or more programming instructions that, when executed, will cause the one or more processors to solve the model comprise one or more programming instructions that, when executed, cause the one or more processors to:
         apply a limit to the opponent model such that the medical condition is able to look ahead at most a set number of steps in the game, and
         create a path for the medical condition in which a sequence of steps includes one or more steps within the set number that are attractive to the medical condition, and at least one step beyond the set number that is associated with a state of the medical condition that is better for the treater, a patient with the medical condition, or both.

2. The system of claim 1, wherein the one or more programming instructions that, when executed, will cause the one or more processors to solve the model comprise one or more programming instructions that, when executed, cause the one or more processors to generate one or more contingent plans in the model.

3. The system of claim 1, wherein the treatment plan comprises randomization via behavioral or mixed strategies.

4. The system of claim 1, wherein the one or more programming instructions that, when executed, cause the one or more processors to solve the model to generate the treatment plan for the medical condition comprise one or more programming instructions that, when executed, will cause the one or more processors to:
   generate the treatment plan to comprise one or more traps, where the medical condition is likely to take actions so as to fall into a trap that causes the medical condition to go into one or more of the following:
      a state in which the medical condition may be more easily treated;
      a state in which the medical condition is less virulent;
      a state in which the medical condition is less contagious; or
      a state from where the medical condition is less likely to evolve into a harmful state.

5. The system of claim 1, wherein the one or more possible treatment actions that a treater can take to treat the medical condition comprise one or more possible treatment actions that a treater can take to treat the medical condition at an individual level, a molecular level, or a population level.

6. The system of claim 1, wherein the instructions to solve the model further comprise instructions to:
   apply a game-solving algorithm that represents the possible treatment actions and the possible medical condition conditions as moves in a sequential game in a large state space.

7. The system of claim 1, wherein the one or more possible treatment actions that a treater can take to treat the medical condition comprise one or more of the following:
   treating the medical condition at a molecular level via a de novo drug;
   prescribing or administering one or more drugs to a patient having the medical condition;
   performing a surgical procedure on the patient having the medical condition;
   applying a therapy to the patient;
   prescribing a lifestyle change to the patient;
   admitting the patient to a treatment facility;
   releasing the patient from the treatment facility;
   taking one or more measurements of the patient; or
   taking no action.

8. The system of claim 6, wherein:
   the sequential game further represents one or more possible nature actions that a nature player may take relating to treatment of the medical condition as moves in the sequential game, wherein each possible nature action is associated with a probability; and
   the model represents occurrence of the possible treatment actions, the possible medical condition actions, and the possible nature actions in the one or more sequences.

9. The system of claim 1, wherein the one or more programming instructions that, when executed, will cause the one or more processors to solve the model comprise one or more programming instructions that, when executed, cause the one or more processors to solve the model using one or more game theory solution concepts and one or more utilities that are associated with outcomes, intermediate states, or transitions in sequential game play.

10. The system of claim 1, wherein the one or more programming instructions that, when executed, will cause the one or more processors to solve the model further comprise one or more programming instructions to implement an opponent exploitation technique.

11. The system of claim 1, wherein the computer-readable memory further comprises one or more programming instructions that, when executed, will cause the one or more processors to use information learned while using results of the model to develop an updated model.

12. The system of claim 1, wherein the one or more programming instructions that, when executed, will cause the one or more processors to solve the model comprise one or more programming instructions that, when executed, cause the one or more processors to compute a best-response strategy to the opponent model using stochastic programming, wherein the use of stochastic programming comprises use of one or more of the following:
  sample trajectory-based optimization, or
  a policy gradient algorithm.

13. The system of claim 1, wherein the one or more programming instructions that, when executed, will cause one or more of the processors to solve the model further comprise one or more programming instructions that, when executed, will cause the one or more processors to:
  implement an equilibrium finding technique comprising any of the following: Nash equilibrium, subgame perfect equilibrium, perfect Bayesian equilibrium, sequential equilibrium, trembling-hand perfect equilibrium, extensive-form perfect equilibrium, extensive-form proper equilibrium, admissible strategies, normal form perfect equilibrium, quasi-perfect equilibrium, normal form proper equilibrium, or correlated equilibrium.

14. The system of claim 1, further comprising refining the model by adding a medical condition action that is not in the model.

15. The system of claim 1, wherein solving the model comprises:
  initially assuming that the opponent will behave rationally; and
  adjusting the model based on observed behavior of the medical condition.

16. A method of developing a course of treatment for a medical condition, comprising:
  by a central processing unit of a system:
    identifying a set of possible treatment actions that a treater can take to treat a medical condition, and a plurality of sequences for the actions;
    identifying a model, wherein:
      the model comprises an opponent model, and in which the medical condition is considered to be an opponent to the treater, and
      the model includes a plurality of possible medical condition actions that represent possible responses of the medical condition to one or more of the possible treatment actions, and the model includes information to predict an updated status based on an expected patient response to each of the possible treatment actions; and
    at least in part by a graphics processing unit (GPU) of the system, solving the model to generate a treatment plan for the medical condition, wherein:
      the treatment plan comprises a set of the possible treatment actions, and
      solving the model comprises:
        applying a limit to the opponent model such that the medical condition is able to look ahead at most a set number of steps in the game, and
        creating a path for the medical condition in which a sequence of steps includes one or more steps within the set number that are attractive to the medical condition, and at least one step beyond the set number that is associated with a state of the medical condition that is better for the treater, a patient with the medical condition, or both; and
  outputting a report of the treatment plan.

17. The method of claim 16, wherein solving the model comprises implementing an opponent exploitation technique.

18. The method of claim 16, wherein:
  solving the model comprises applying a game-solving algorithm that represents the possible treatment actions and the possible medical conditions as moves in a sequential game in a large state space; and
  the model comprises one or more utilities that are associated with outcomes, intermediate states, or transitions in sequential game play, wherein the one or more utilities comprise a function of a measurement of one or more of the following:
    health of a patient with the medical condition;
    a cost to the patient, the treater, or a third party payor; or
    a current state of the medical condition.

19. A system for developing a course of treatment for a patient population in an epidemic, comprising:
  one or more processors;
  a user interface;
  a communication port; and
  a non-transitory, computer-readable memory comprising one or more programming instructions that, when executed, will cause one or more of the processors to:
    receive, via the user interface or the communication port, information corresponding to an epidemic that may affect a population,
    identify a set of possible treatment actions that a treater can take to treat a medical condition that arises in the epidemic, and a plurality of sequences for the possible treatment actions, wherein the possible treatment actions comprise a vaccine and quarantining;
    identify a model, wherein:
      the model comprises an opponent model, and in which the medical condition is considered to be an opponent to the treater; and
      the model includes a plurality of possible medical condition actions hat represent possible responses of the medical condition to one or more of the possible treatment actions,
    solve the model to generate a treatment plan for the medical condition, where the treatment plan comprises a set of possible treatment action, wherein solving the model comprises:
      applying a limit to the opponent model such that the medical condition is able to look ahead at most a set number of steps in the game, and creating a path for the medical condition in which a sequence of steps includes one or more steps within the set number that are attractive to the medical condition, and at least one step beyond the set number that is associated with a state of the medical condition that is better for the treater, a patient with the medical condition, or both, and output a report of the treatment plan.

20. The system of claim 19, wherein the medical condition actions also comprises a mutation of a strain of virus that is a cause of the epidemic.

21. The system of claim 19, wherein:

the one or more processors comprise a central processing unit (CPU) and a graphics processing unit (GPU);

the instructions to identify the possible treatment actions and the model are, when executed, implemented by the CPU; and at least some of the instructions to solve the model are, when executed, implemented by the GPU.

* * * * *